United States Patent [19]

Chiba et al.

[11] Patent Number: 5,137,013
[45] Date of Patent: Aug. 11, 1992

[54] JOINT STRUCTURE COMPOSED OF FLEXIBLE TUBING AND A HANDLING APPARATUS COMPRISING SUCH A JOINT STRUCTURES

[75] Inventors: Toshihiko Chiba, Hachiooji; Michihiko Okuzumi, Hino; Tsuneo Kaziwara, Tokyo, all of Japan

[73] Assignee: Olympus Optical Company Limited, Japan

[21] Appl. No.: 721,111

[22] Filed: Jun. 26, 1991

[30] Foreign Application Priority Data

Jun. 29, 1990 [JP] Japan .................................. 2-173281

[51] Int. Cl.$^5$ ................................................ A61B 1/06
[52] U.S. Cl. .......................................... 128/4; 604/282
[58] Field of Search ........................................ 128/4-6,
128/772, 657; 604/282, 283; 267/179, 289, 73;
29/173; 403/229

[56] References Cited

U.S. PATENT DOCUMENTS

| | | | |
|---|---|---|---|
| 3,890,687 | 6/1975 | Goldberg | 29/173 |
| 4,889,327 | 12/1989 | Seyler | 267/289 X |
| 4,899,787 | 2/1990 | Ouchi et al. | 128/4 X |
| 5,002,041 | 3/1991 | Chikama | 128/4 |
| 5,069,674 | 12/1991 | Fearnot et al. | 604/282 |

Primary Examiner—Robert Bahr
Assistant Examiner—J. Doyle
Attorney, Agent, or Firm—Bruce L. Adams; Van C. Wilks

[57] ABSTRACT

The joint structure of the present invention includes a flexible tube constructed of a coil-wound metal wire element and of another member. This other member includes 1) a main joint joining the end of the outer peripheral surface of the flexible tube to the end of the other member by laser welding either part or all of the main joint; and 2) spot welds joining together adjacent turns of the coil in the vicinity of the main joint by irradiating a laser beam onto a plurality of separate spots extending over the adjacent turns. A handling device for use in endoscopes having such a structure and a similar structure, in which the other member is also a flexible tube either softer or harder than the above flexible tube, is also discussed. Adjacent turns of the coil in the vicinity of each of the welded joints are laser spot-welded at a number of spots, thereby strengthening the thermally affected regions during the laser welding of the joints and increasing the rigidity of the region. This compensates for the lowering of the elastic limit in the vicinity of the welded joints, thereby preventing plastic deformation or buckling in the flexible tubes in the thermally affected regions under a strong bending force.

19 Claims, 13 Drawing Sheets

JOINT STRUCTURE COMPOSED OF FLEXIBLE TUBING AND A HANDLING APPARATUS COMPRISING SUCH A JOINT STRUCTURES

BACKGROUND OF THE INVENTION

The present invention relates to a joint structure composed of flexible tubing and a handling apparatus constructed of such a joint structure for use in endoscopes. The joint structure composed of flexible tubing joins to another member. Specifically, the present invention relates to a joint structure consisting of one soft flexible tube and one hard flexible tube joined together by laser welding, and also to a flexible tube and a leading metal member joined together by laser welding.

As shown in FIG. 14, conventional forceps with endoscopes, are inserted through a forceps inlet (12) provided on an endoscope manipulator means (11). The forceps go through an insertion channel (not shown) stored within both a connection part (13) and a bendable part (14), and protrude from a forceps outlet (16) provided at the head (15) of the endoscope (10). At the leading edge, the forceps comprise, a pair of forceps cups (8) that are operated using a forceps manipulator means (21).

As shown in FIGS. 14 and 15, the forceps (17) comprises flexible tubing constructed of a coil-wound metal wire element that can be inserted through an insertion channel in the endoscope (10); and a flexible tubing support member (22) consisting of a forceps manipulator means (21), and a leading metal member (7) that has a pair of forceps cups (8) attached through an attachment pin (9) for opening and shutting the forceps cups (8), to the leading metal member (7). The support member (22), that is a part of the forceps manipulator means (21), connects through an excessive-bend preventor coil (20) to the base end (19) of the flexibble tube (18). The pair of forceps cups (8) connects to the leading end of an operation wire (25) through a pair of linking means (23) having a pair of back linking parts (24) protruding from the linking means (23), a pair of links (24') connected to the back linking parts (24), and a wire joint metal member (26). Numerals 27 and 28 are attachment pins for connecting the links (25). The base end of the operation wire (25) connects to an operation control (29) composing the forceps manipulating means (21).

When operating conventional forceps for endoscopes, the thumb is inserted into a hole bored in the flexible tubing support member (22), and the operation control (29) is held with the second and third fingers, so that relative movement between the operation control (29) and the support member (22) causes the forceps cups to open and shut.

When inserted in a body cavity, the bendable part (14) can be manipulated so that the leding end (15) can be pointed towards the body part that needs to be observed. The connector (13) is relatively elastic, and is flexible enough to facilitate insertion of the leading end (15) and the bendable part (14). The connector (13) also rotates together with the entire forceps manipulator means (11). Accordingly, the bendable part (14) can be bent at sharp angles, and the connector (13) is flexible with a somewhat low degree of curvature. The insertion channel stored within the two parts 14 and 13 has the same degrees of curvature at respective portions in accordance with the bending of the two parts 14 and 13.

In exactly the same way, the flexible tube (18) of the forceps for an endoscope (17) also has the same degrees of curvature ass the insertion channel. Accordingly, the flexible tubing (18) has: (a) a soft flexible tube (1) that bends in line with the bendable part (14); and (b) a hard, flexible, elastic tube (2) that follows the movement of the connector (13).

One way to form a flexible tube for use in a forceps device for an endoscope is to join and integrate the soft flexible tube (1) and the hard flexible tube (2). As shown in FIG. 16, each tube is made of metal wire elements, though the diameters and having an equal outside diameter. To join the two flexible tubes, the end face of each flexible tube is flattened, and the flexible tubings are butted face to face. The tubes are then welded together by irradiating a laser beam (31) onto the outer surface of the butted joint and forming a weld joint (3) on the whole of the outer surface, as shown in the section of the welded connection given in FIG. 17.

A conventional method for joining the flexible tube (1) and the leading metal member (7) is disclosed in Japanese Patent Publication No. 246741/1985. The method is schematically shown in FIG. 18. As shown in this figure and also in FIG. 19 (that depicts a section of the welded joint), either the soft flexible tube (1) or the leading metal member (7) is worked so that the flexible tubing (1) into the metal member (7). The tube and leading mumber are they welded together by irradiating a laser beam (31) onto the outer surface of the butted joint and forming a weld joint (3) on the whole of the outer surface. In this conventional method, the flexible tubing is made up of a metal wire element having a high corrosion resistance (e.g., stainless steel wire such as SUS 304-WPB for use in springs) wound in to a coil.

In the prior art, the austenitic stainless steel (represented by SUS 304) is not hardened by quenching. Work strain can be removed by decomposing chromium carbide by means of a solid-solution quenching from a high temperature (1010°–1150° C. in the case of SUS 304). Alternatively such austenitic steel can be hardened and its mechanical strength can be raised by strong cold working.

SUS 304-WPB is a metal wire element for use in the above-described flexible tubing and is manufactured by strongly cold-drawing a wire element of austenitic stainless steel SUS 304 after a solid solution treatment. Its hardness and mechanical strength are larger than those of SUS 304 wire heat-treated for solid solution but not cold-drawn.

In laser welding, the weld is heated above the melting point and the surrounding area is heated at a fairly high temperature. Accordingly, the weld and the surrounding area are annealed during welding and while cooling, and have significantly low mechanical strength—much lower than that of the SUS 304-WPB wire element.

Although the above description concerning the thermal effect during welding has been made with reference to austenitic stainless steel SUS 304, it is clearly understood that the same is by way of illustration and example only and is not to be taken by way of limitation. Rather, the description is applicable to any materials mechanically strengthened by work-hardening. In general, metal wire elements for constructing flexible tubings (or coil springs) include various kinds of stainless steel wire, hard steel wire, piano wire, oil-tempered wire, and many others. Work-hardening raises the mechanical strength of most of these elements during cold-drawing, but heating lowers it during welding.

FIG. 20 shows an appearancce of the welded joint and surounding area, corresponding to the section of the welded joint of the soft flexible tube (1) to the hard flexible tube (2) shown in FIG. 17. FIG. 21 shows the welded joint and surrounding area correspondig to the welded joint of the soft flexible tube (1) to the leading metal member (7) shown in FIG. 19. In FIGS. 20 and 21, reference numerals 3 is the welded joint and 4 is the region thermally affected by laser welding. The range of the thermally affected region depends on the heat input by the laster beam, the diameter of the metal wire element composing the flexible tube (1), and other factors. In the above-described conventional laser welding, the thermally affected regions (4) have been annealed during the after welding, so their elastic limits are much lower than other portions of the flexible tube.

As shown in FIG. 22, when manipulating forceps for an endoscope, the welded joints (3) and their neighboring portions are bent or buckled to small radii by forces (32 and 33)—for example, when the user inserts the forceps forcefully through the forceps inlet in the face of resistance, or when the user handles the forceps with excessive force. In such cases, as shown in FIGS. 23 and 24, the thermally affected regions (4) are subject to plastic deformation or buckling and od not recover their original shape. In the particular case of a joint structure comprising a soft flexible tubing (1) and a hard flexible tubing (2), as shown in FIG. 23, both the wire element diameter and elastic limit of the soft flexible tube are lower than those of the hard flexible tube, and hence plastic deformation or buckling occurs more often in the thermally affected region of the soft flexible tube.

SUMMARY OF THE INVENTION

One objective of the present invention is to eliminate the above disadvantage in the conventional handling apparatus for use in endoscopes.

Another objective of the present invention is to provide a joint structure composed of flexible tubing which is manufactured using laser welding and does not suffer from lowered elastic limits and hence is unlikely to plastically deform or buckle.

A further objective of the present invention is to provide a handling apparatus constructed of such a joint structure for use in endoscopes.

The joint structure of the present invention consists of both flexible tubing constructed of a coil-wound metal wire element and another member. This other member comprises 1) a main joint joining the end of the outer peripheral surface of the flexible tubing to the end of the other member by laser welding either the whole or part of the main joint; and 2) spot welds that join adjacent turns of the coil in the vicinity of the main joint by irradiating a laser beam onto a number of separate spots extending over the adjacent turns.

The handling apparatus for use in endoscopes of the present invention comprises one soft flexible tube and hard flexible tube. Both the hard and soft tubes are constructed of a coil-wound metal wire element. The outer end of each element is joined together by laser welding, and adjoining turns of the coil of at least the soft flexible tube are joined together by means of laser spot welding at a number of spots. These adjoining turns include that at the joined surface tip.

The present invention also includes a handling apparatus for use in endoscopes. This apparatus comprises a flexible tube constructed of a coil-wound metal wire element and a leading metal member, in which the outer tip of the flexible tube and the leading metal member are joined together by laser welding, and in which adjoining turns of the coil of the flexible tube are joined together by means of laser spot welding at a number of spots. The adjoining turns include that found at the joined tip of the flexible tube.

According to the above construction of the joint structure comprising both a flexible tube made of a coil-wound metal wire element and another member and to the above construction of the handling apparatus comprising such a structure for use in endoscopes, laser spot welding of adjoining metal turns of the coil in the vicinity of the welded joint at a plurality of spots strengthens and increases the rigidity of thermally affected regions. This compensates for the lowering of the elastic limit in the vicinity of the welded joint, thereby preventing plastic deformation or buckling in the thermally affected region when the flexible tube is subjected to a strong bending force.

The handling apparatus comprising the above joint structure for use in endoscopes is significantly resistant to plastic deformation and buckling in the vicinity of the welded joints between the soft and hard flexible tubes and between the flexible tube and the leading metal member, even when subjected to strong being forces—as when inserting the handling apparatus through the forceps inlet of the endoscope, or when looping the handling apparatus for the purpose of carrying or sterilizing it.

These objects and other objects, features, aspects, and advantages of the present invention will become more apparent from the following detailed description when taken in conjunction with the accompanying drawings.

DETAILED DESCRIPTION OF THE PREFERRED EMBODIMENTS

First Embodiment

Figure 1:
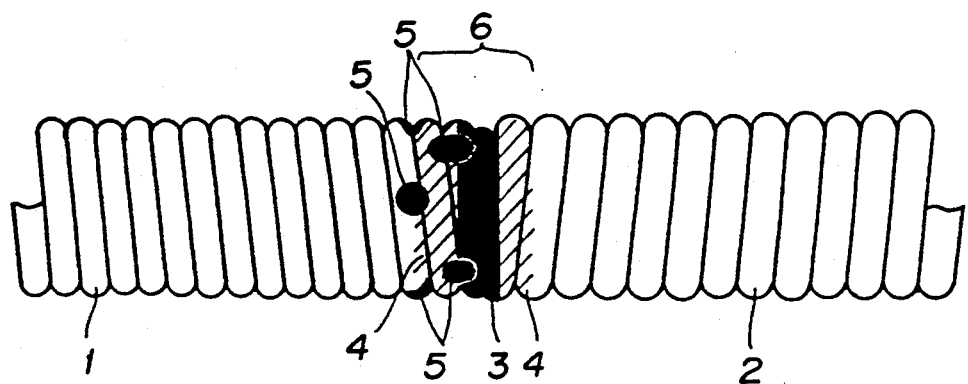
FIG. 1 is an enlarged section showing the first embodiment of the present invention from above. The figure shows a joint structure constructed of soft and hard flexible tubes in the vicinity of the welded joint.
Figure 2:
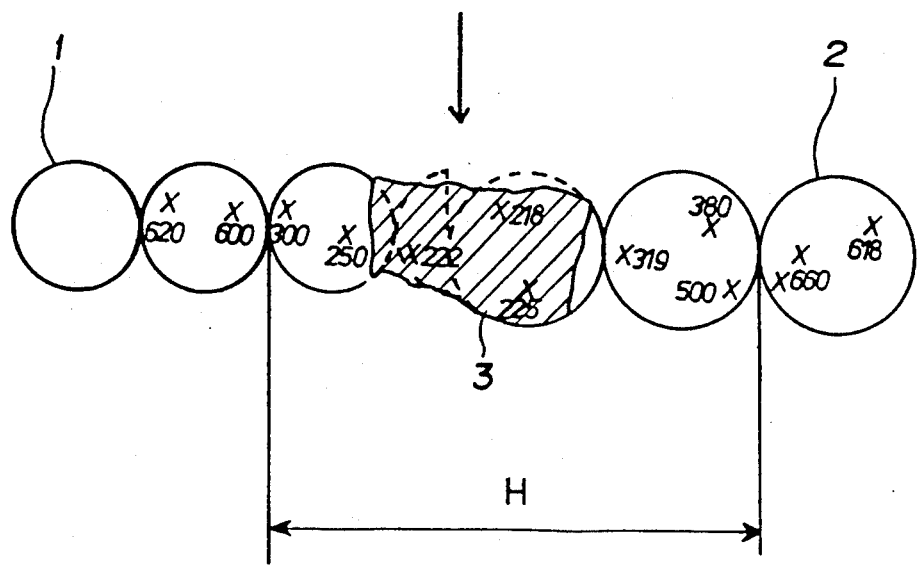
FIG. 2 presents measurements values for Vickers hardness in and around the welded joint of the joint structure of the first embodiment of the present invention.

FIG. 1 is an enlarged, raised section showing the joint structure—constructed of soft and hard flexible tubes—in the vicinity of the welded joint of the first embodiment of the present invention. FIG. 2 gives rough measurement values of Vickers hardness in and around the welded joint of the joint structure of the first embodiment of the present invention.

Referring to FIG. 1, reference numeral 1 indicates a soft flexible tube that is joined to a hard flexible tube (2). In joining and integrating the two flexible tubes, (1 and 2), the end face of each of the flexible tubes is flattened, and then the flexible tubes are butted face to face and welded together b irradiating a laser beam (31) onto the outer surface of the butted joint while rotating the two flexible tubes together and forming a welded joint (3) on the whole of the outer surface.

Reference numeral 4 indicates a thermally affected region, which has been heated during laser welding and hence has lowered its mechanical strength and elastic limit. After axially moving the joined tubings a small distance, the metal wire element portion of the soft flexible tubing (1) corresponding to the thermally affected region is laser spot welded at four separate spots (5) while rotating the joined tubings by one turn. Then, after further moving the connected tubings axially a small distance, the same spot-welding procedure is repeated, to form more spot welds (5).

in the first spot welding step, the turn of metal wire element of the soft flexible tube (1) belonging to the welded joint (3) has been spot-welded to the adjoining turn of the metal wire element of the soft flexible tube (1) at four separate positions. Reference numeral 6 indicates a rigid region, i.e., that portion of the thermally affected region (4) which is reinforced by the spot welds.

The range of the thermally affected region depends on the amount of heat imparted to to the welded joint by the laser beam. Accordingly, if the amounts of heat are equal, the ranges are the same provided that other conditions are identical. If the diameter of the metal wire element varies, the range changes.

FIG. 2 shows measurements of Vickers hardness on the surface of a section of a joint structure constructed of both soft flexible tubes (1) 1.6 mm in outside diameter using a metal wire element 0.4 mm in diameter and a hard flexible tube (2) 1.6 mm in outside diameter using a metal wire element 0.5 mm in diameter in the vicinity of the welded joint (3). The welded joint was laser welded by using a YAG laser under the following conditions: laser enlargy=2.4 J. oscillation frequency=10 Hz, spot diameter=0.5 mm, rotation speed of the flexible tube=14000 degrees/min or ca. 38.8 RPM. In FIG. 2, reference symbol H indicates the range of the thermally affected region (4). Since the coils of the metal wire element compose the flexible tubings, the arrangement of metal wire elements in a section, and hence the range (H), varies with the direction of the cut plane. Accordingly, to obtain the range (H) exactly, it is necessary to measure the hardness on a number of sectional planes.

In a conventional joint structure constructed of a soft flexible tube and a hard flexible tube, when the metal wire element of the soft flexible tube is significantly smaller in diameter and hence in elastic limit than that of the hard flexible tube, strong bending of the joint structure in the vicinity of the welded joint causes the soft flexible tube to deform plastically.

On the other hand, in the joint structure of the first embodiment, separate spot welds made by a laser beam in and outside the thermally affected region (4) have resulted in the joining of adjoining turns of the coil of the soft flexible tube at a number of positions, and hence the thermally affected region (4) has been strengthened on the soft flexible tube side, an is an strong as the rigid region (6). Accordingly; under a strong bending force, it is not the rigid region (6) but some other portion of the soft flexible tube (1) that buckles. The spot welds are so small and so separate from each other that they do not cause a significant lowering of elastic limit in and around the rigid region (6).

According to the first embodiment, the joint structure composed of flexible tubes and manufactured by laser welding is not subject to lowering of its elastic limit and hence is unlikely to deform or buckle plastically. The joint is therefore suitable for endoscope handling devices.

Figure 3:
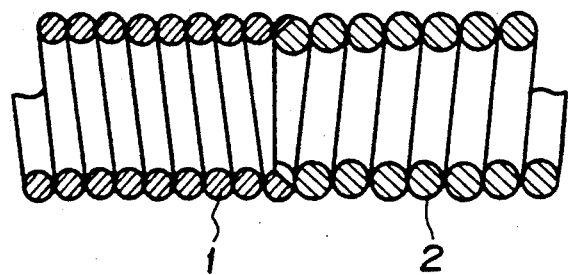
FIGS. 3 and 4 are enlarged sections showing different connections that can be used in the joint structure of the first embodiment of the present invention.
Figure 4:
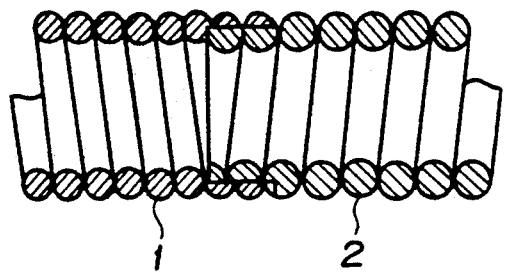

The first embodiment of the present invention is not limited to a joint structure in which the end faces of both the soft flexible tube (1) and the hard flexible tube (2) are flattened before being joined by laser welding, but is applies widely to a joint structure in which the end faces of the soft flexible tube (1) and the hard flexible tube (2) are carefully fit together. For example, the end face of one flexible tube may be convexly tapered while that of the other may be concavely tapered, as shwon in FIG. 3. A further example is given in FIG. 4, where the end face of one flexible tube in convexly stepped and that of the other is concavely stepped so that the two end faces fit perfectly together.

Although the two flexible tubes were welded together before having spot welds in the joint structure of the first embodiment, the opposite order is also possible—that is, spot welds are made first and the welded joint is made afterwards.

Furthermore, spot welds may be positioned at any spot that strengthens the thermally affected region (4) and increases its rigidity. Although, in FIG. 1 showing the joint structure of the first embodiment, there were four spot welds (5) in each of the two ciecles separated from each other, there may be another number of spot welds—for example, two, three, five, etc. If the thermally affected region (4) is narrow, there may be only one circle containing a number of spot welds (5), in so far as they lie over the adjoining two turns of the metal wire element, including the turn composing the welded joint (3).

Figure 5:
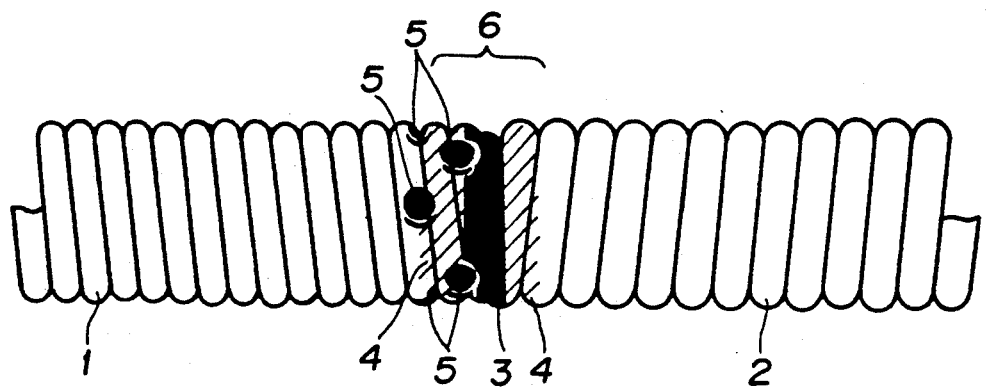
FIGS. 5 through 7 are enlarged and raised sections showing different arrangements of laser spots in the vicinity of the welded joint of the joint structure of the first embodiment of the present invention.

Although no laser spot overlaps with any other laser spot on the outer surface in FIG. 1 for the joint structure of the first embodiment, two laser spots may overlap with each other to form elongated spot welds, as shown in FIG. 5, where four of such elongated spot welds are visible (one of the welds is partly visible). Instead of two laser spots, three or more laser spots may overlap with one another to form a more elongated spot weld so long the elongated spot weld does not thermally affect the region surrounding it.

Figure 6:
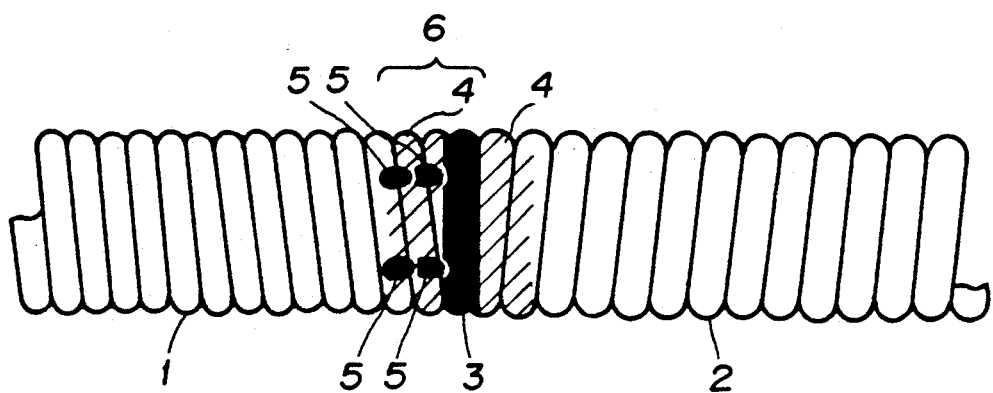

As shown in FIG. 6, the major axes of elongated spot welds may be in the axial direction of the flexible tubings.

Figure 7:
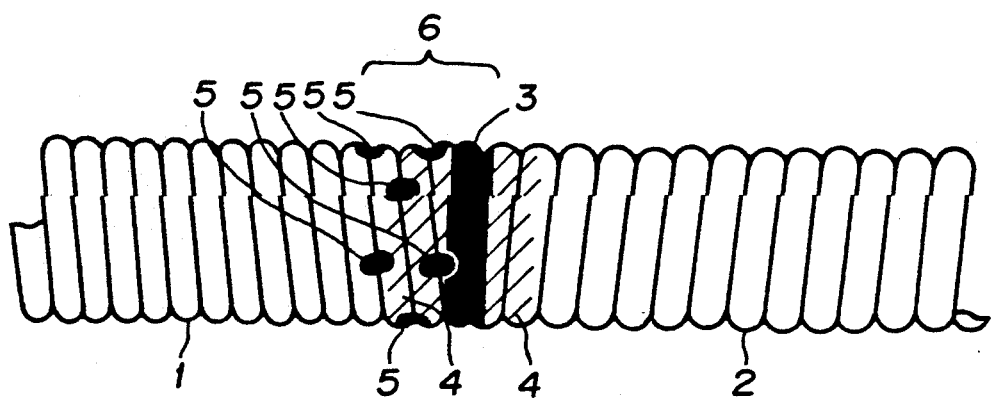

As shown in FIG. 7, every spot weld may be placed along the contact line between adjoining turns of the coil. This can be done by making laser spot welds discontinuous along the above contact line while rotating around the axis of the flexible tubings and at the same time moving the flexible tubings axially at such speeds that the spot welds are placed along the contact line. Furthermore, in addition to these spot welds, additional spot welds may be placed so that the additional ones may overlap with some or all of the above spot welds so long as the overlaping spot welds do not thermally affect the region surrounding them.

The first embodiment of the present invention is not limited to a joint structure in which both the soft flexible tube (1) and the hard flexible tube (2) are coils of the same outside diameter constructed of metal wire elements of different diameters, but applies to any joint structure constructed of two flexible tubes having other relationships between the soft and hard flexible tubes than those given in the above description of the first embodiment of the present invention as long as one of the two flexible tubes is soft and the other is hard.

Figure 8:
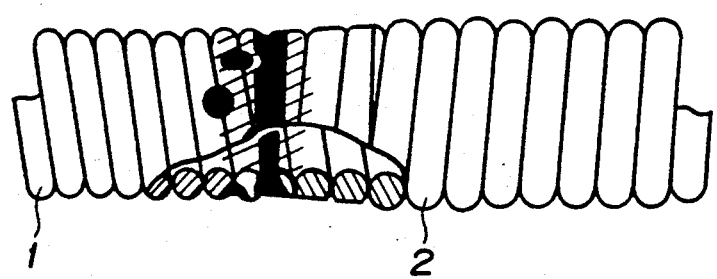
FIGS. 8A, 8B, 8C and 8D are enlarged, raised sections showing different combinations of soft and hard flexible tubing in the vicinity of the welded joint of joint structure of the first embodiment of the present invention.
Figure 8:
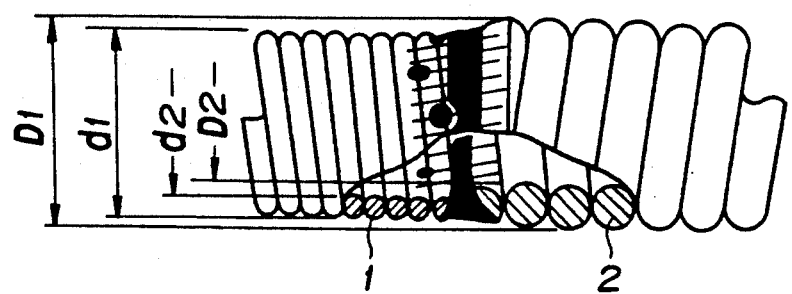
Figure 8:
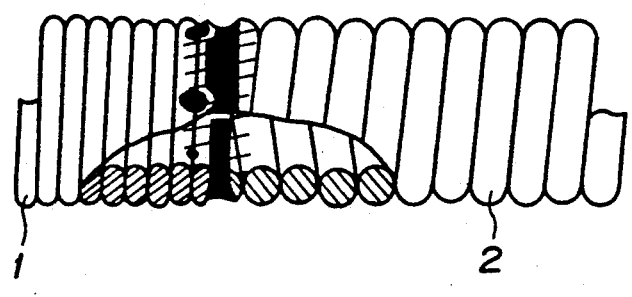

For example, in the above-described construction of a joint structure of the first embodiment, the soft flexible tube (1) and the hard flexible tube (2), instead of having an equal outside diameter, may have an equal inside diameter, as shown in FIG. 8(A), provided that the hard flexible tube, which originally had a larger outside diameter, is tapered by grinding work to have an outside diameter equal to that of the soft flexible tube at their joint before their adjacent faces are flattened, butted, and joined by laser welding.

Similarly, the first embodiment of the present invention applies even to a joint structure in which the outside and inside diameter ($d_1$ and $d_2$) of the soft flexible tube (1) differ, respectively, from those ($D_1$ and $D_2$) of the hard flexible tube (2), provided that the hard flexible tube (2), which originally had a larger outside diameter, is chamfered so as to have a diameter equal to that of the soft flexible tubing (1) at their joint, as shown in FIG. 8(B).

Also, the first embodiment of the present invention applies to a joint structure in which the soft flexible tube (1) and the hard flexible tube (2) have equal outside and inside diameters but have metal wire elements of different sectional configurations—for example, as shown in FIG. 8(C), an oval shape for the soft flexible tube (1) and a circular shape for the hard flexible tube (2). Furthermore, the metal wire element for the coil may have any sectional shape in addition to circular and oval. (e.g., quadrangular) so as to alter the flexibility of the coil made of the metal wire element.

Figure 8D:
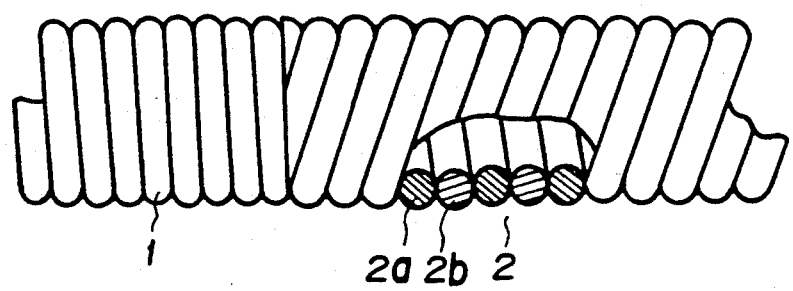

Futhermore, the soft flexible tube (1) or the hard flexible tube (2) may be constructed of, instead of a single metal wire element, a number of metal wire elements—for example, as shown in FIG. 8(D), two metal wire elements (2a and 2b) for the hard flexible tubing (2) (the welded joint (3) is not shown).

Figure 9:
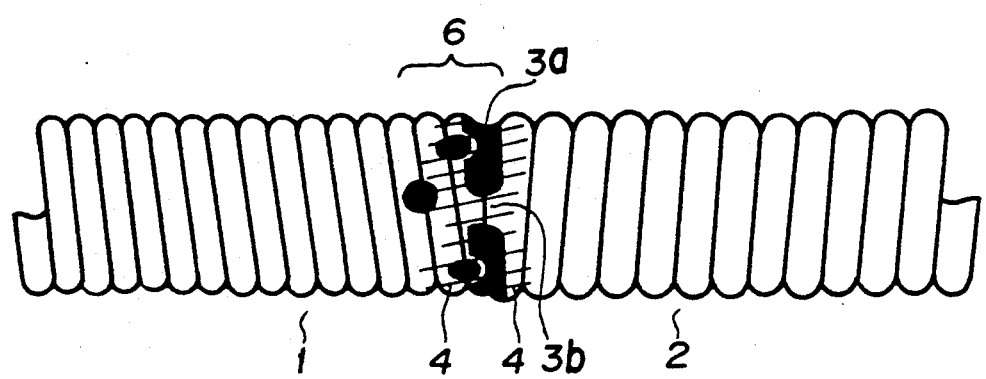
FIG. 9 is an enlarged section view showing the first embodiment of the present invention from above. The figure shows the welded joint of a joint structure constructed of soft and hard flexible tubes and is identical to FIG. 1 except for the welded joint.

Furthermore, the first embodiment of the present invention is not limited to the joint structure shown in FIG. 1, in which the joint of the two flexible tubings is continuously welded by continuously irradiating a laser beam on the circumferential surface of the joint, but applies also to a joint structure, as shown in FIG. 9, that consists of a continuous laser-welded joint (3a) and an unwelded portion (3b). In this case, the unwelded portion helps diminish the range of the thermally affected region because the duration of laser welding is shorter than that for the fully continuous welded joint shown in FIG. 1.

The diameters of metal wire elements and the outside diameters of coils made of the metal wire elements are not limited to those shown in FIG. 2; other suitable sizes may be used. In a conventional handling apparatus constructed of a joint structure composed of flexible tubing for use in an endoscope, the soft flexible tube is in many cases a coil 1.2-3.3 mm in outside diameter made of a metal wire element 0.2-0.55 mm in diameter; the hard flexible tube is selected in relation to the soft flexible tube and is in many cases a coil of 1.25-3.6 mm in outside diameter made of a metal wire element 0.3-0.7 mm in diameter. However, the present invention is not limited to the above sizes.

Second Embodiment

Figure 10:
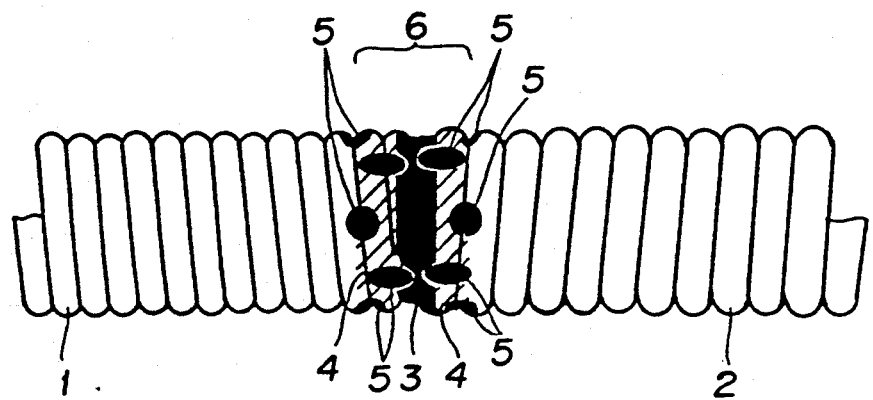
FIG. 10 is an enlarged section view showing a second embodiment of the present invention from above. The figure shows the welded connection of a joint structure constructed of soft and hard flexible tubes.

FIG. 10 is an enlarged, raised secion showing a second embodiment of the present invention. The figure shows a joint structure constructed of soft and hard flexible tubes welded together.

In the second embodiment, laser spot welding is performed to form spot welds (5) on the thermally affected region (4) of the hard flexible tube (2). The other construction of the second embodiment is the same as that of the first embodiment and therefore description thereof is omitted. The same reference numerals are given to members that are the same in both embodiments.

In this embodiment, the outer surface of the thermally affected region (4) of the hard flexible tube (2) is spot-welded in a way similar to the first embodiment by a laser beam at such separate positions that adjoining turns of the coil composing this flexible tube in the region (4) are connected together at these positions and are strengthened and become rigid. As in the first embodiment, spot welds (5) at the above separate positions form a rigid region (6).

When a sufficiently strong bending force acts on the welded joint between the soft flexible tube (1) and the hard flexible tube (2) of the first embodiment, the hard flexible tube (2) plastically deforms at the thermally affected region (4).

In the second embodiment, on the other hand, the thermally affected regions (4), whose elastic limit has lowered after laser welding, of the soft flexible tube (1) and the hard flexible tube (2) have become as rigid as rigid region (6) owing to the separate laser spot welds on the outer surface of both regions. Therefore, a strong bending force acting on the welded joint does not cause a buckling of the rigid region (6), but instead, failure occurs at some other portion of the two flexible tubes. It is noted that the separate spot welds forming the rigid region (6) do not have a significant thermal effect on the neighborhood of the rigid region (6), and so do not lower the region's elastic limit.

According to the second embodiment, the joint structure composed of flexible tubing and manufactured by means of laser welding is not subject to lowering of its elastic limit and so is unlikely to deform or buckle plastically. The joint is therefore suitable for endoscope handling devices.

When manufacturing the joint structure, it does not matter whether the laser welding done to join the two flexible tubes precedes or follows the spot welding. Furthermore, the spot welds may be positioned any place that strengthens and the thermally affected region and increases its rigidity.

Third Embodiment

Figure 11:
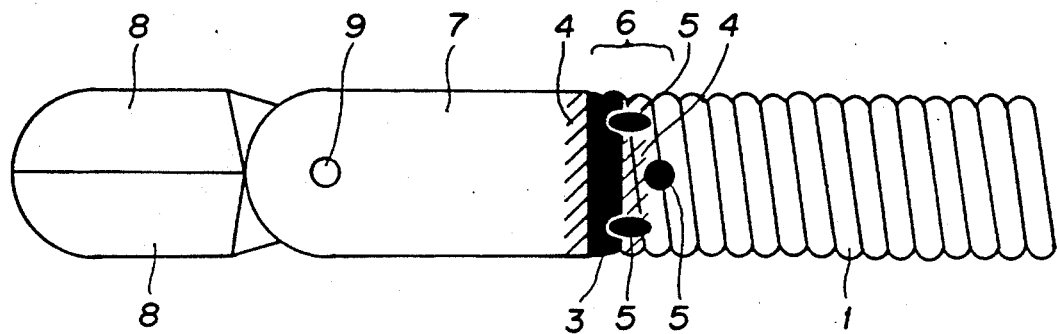
FIG. 11 is an enlarged section view showing a third embodiment of the present invention from above. The figure shows the welded connection of a joint structure constructed of a soft flexible tube and a leading metal member.

FIG. 11 is an enlarged, raised section of a third embodiment of the present invention. The figure shows the welded joint of a soft flexible tube with a leading metal member.

Reference numeral 7 is a leading metal member having a pair of forceps cups (8) attached—through an attachment pin (9) for opening and shutting the forceps cups (8)—to the leading metal member 7. A laser beam has been irradiated onto the outer butted portion of the fitting joint of the soft flexible tube (1) with the leading member (7) to weld them together and form a welded joint (3), thereby integrating the leading metal member (7) with the soft flexible tube (1). Before laser welding, the flexible tube had been inserted and engaged into the leading member by working either the leading member or the flexible tubing.

In FIG. 11, the shaded portion (4) is thermally affected by the heat imparted by the laser beam. In this region, both the mechanical strength and elastic limit are lower than any other portion. After completing laser welding on the above outer surface, the laser beam is used to spot-weld the outer surface of the thermally affected region of the soft flexible tube (1) at separate positions so as to join adjacent turns of its coil, thereby strengthening and the thermally affected region (4) and increasing its rigidity. Reference numeral 5 indicates spot welds. Reference numeral 6 indicates a rigid region that has been strengthened by the spot welds joining together the above adjacent turns of the coil.

In the above construction of the joint structure of this embodiment, the thermally affected region (4), whose elastic limit has been lowered by laser welding, of the soft flexible tube (1) has been made as rigid as the rigid region (6) owing to separate laser spot welds on the outer surface of the region. Therefore, a strong bending force acting on the laser-welded joint does not cause buckling of the rigid region (6), which contains the thermally affected region (4). Instead, failure occurs at some other portion of the flexible tubing.

The spot welds forming the rigid region (6) are separate and few in number. Therefore, they do no impart a significant thermal effect on the neighborhood of the rigid region (6), and so do not lower the elastic limit thereof.

Accordingly, laser welding is applicable to the manufacturing of a joint structure composed of flexible tubing and a leading metal member without lowering the elastic limit of the neighborhood of the welded joint. Therefore, such a joint structure is unlikely to deform or buckle plastically; it is thus suitable for handling devices used with endoscopes.

When manufacturing the joint structure of the third embodiment, as in the first and second embodiments, it does not matter whether the laser welding done to join the flexible tube with a leading metal member precedes or follows the spot welding. Furthermore, the spot welds may be placed anywhere that strengthens the thermally affected region and increases the region's rigidity.

In FIG. 11, the leading metal member (7) is inserted and engaged into the soft flexible tubing (1). Instead, a soft flexible tube (1) may be inserted and engaged into a leading metal member (7), as shown in FIG. 12, before forming a welded joint (3) and then making spot welds (5) between adjoining turns of the coil composing the flexible tubing.

Figure 12:
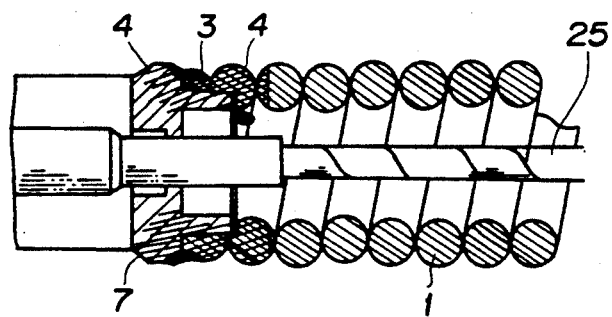
FIGS. 12 and 13 are enlarged sectional views showing different joint types of the joint structure in the third embodiment of the present invention.
Figure 13:
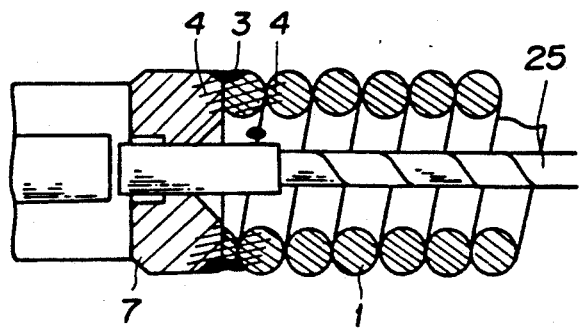
Figure 14:
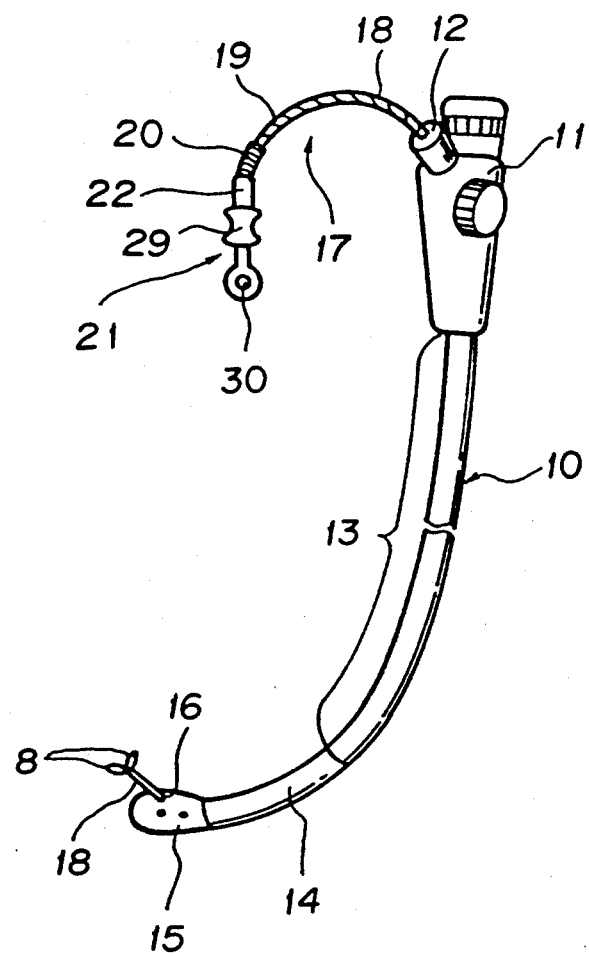
FIG. 14 is a perspective view showing a conventional forceps inserted in an endoscope.
Figure 15:
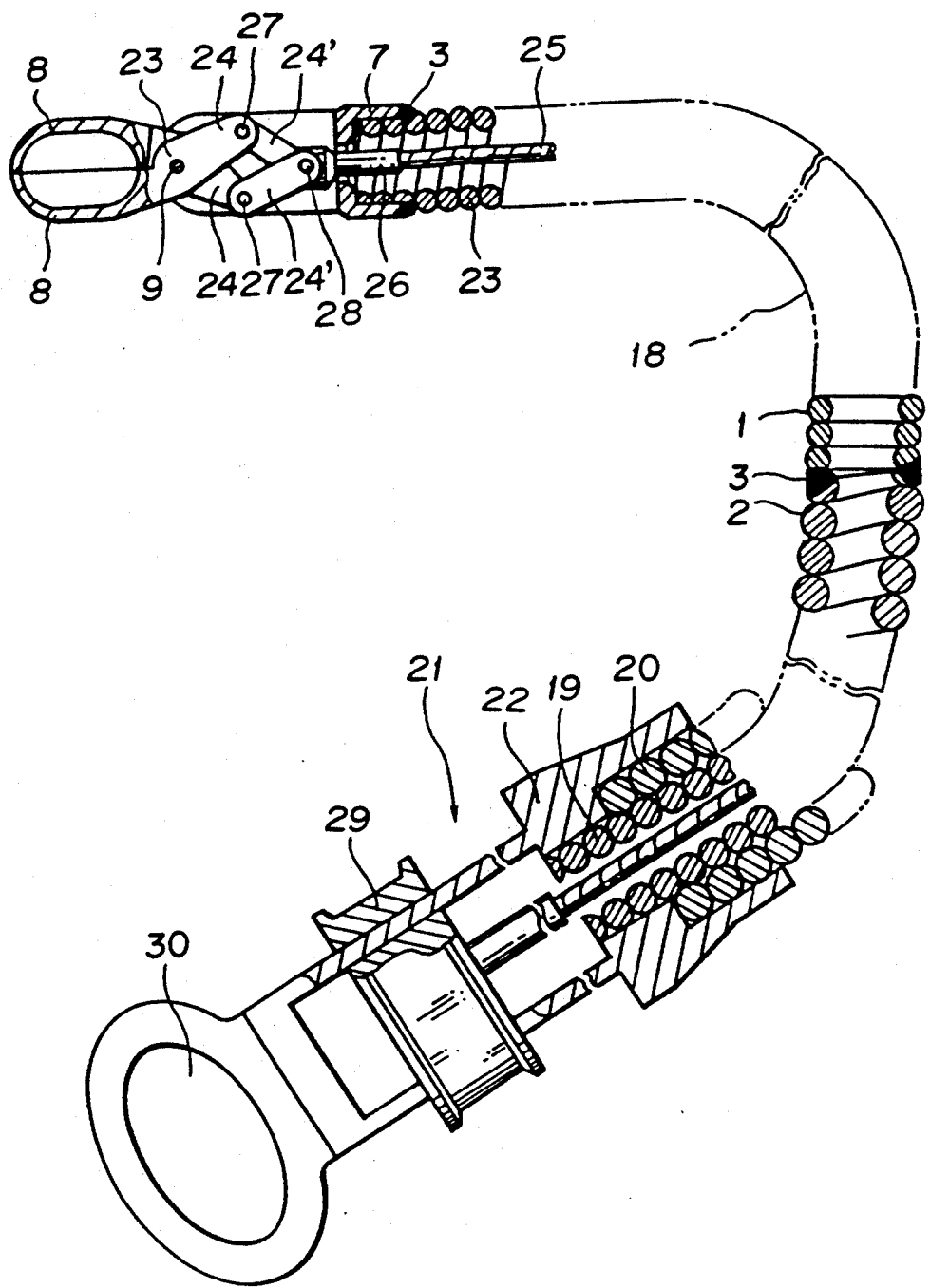
FIG. 15 is an elevated, partial section view showing a conventional forceps.
Figure 16:
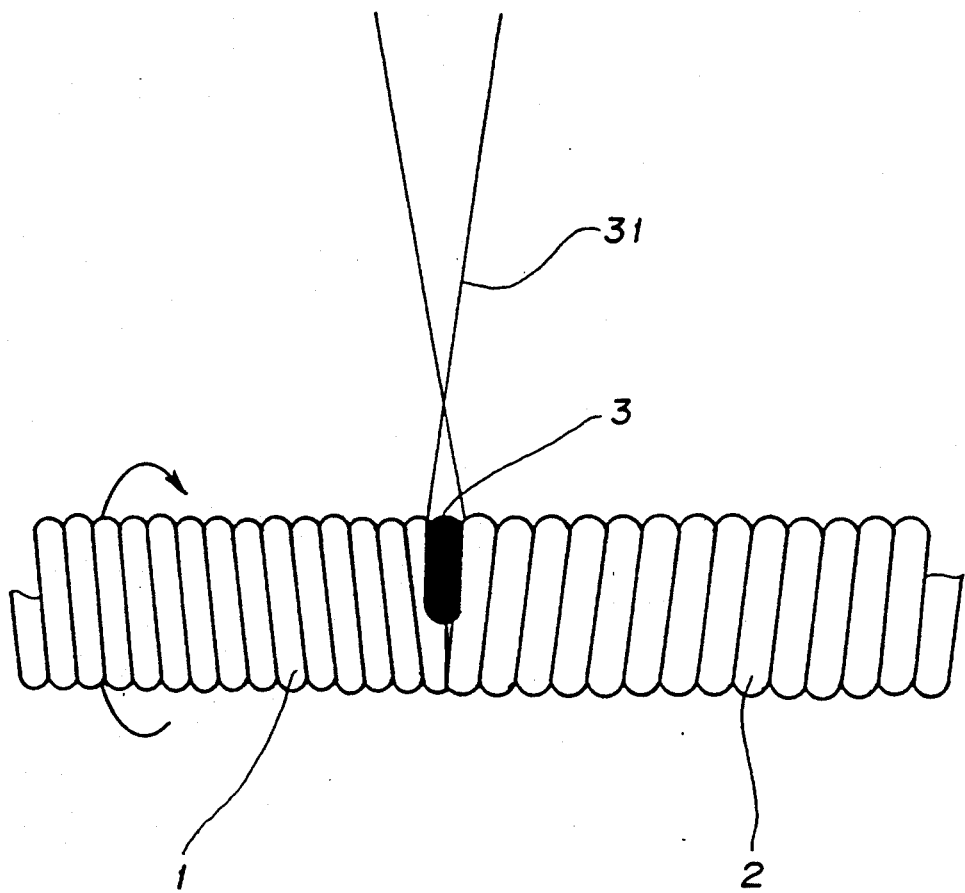
FIG. 16 is an enlarged, elevated section view showing a conventional forceps.
Figure 17:
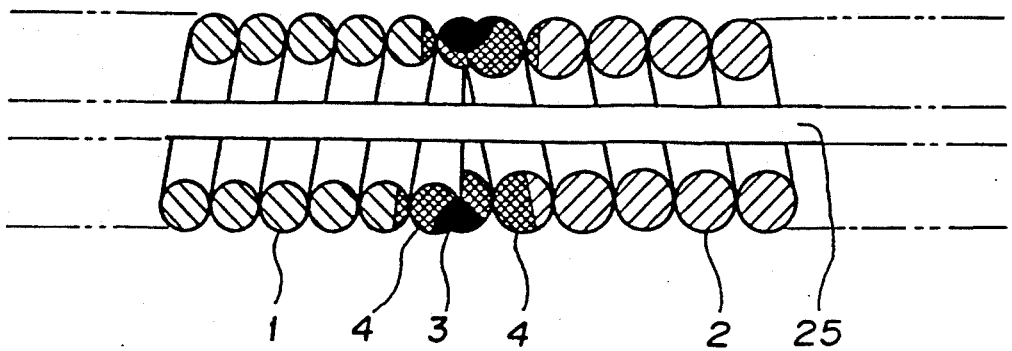
FIG. 17 is an enlarged section view showing a conventional forceps.
Figure 18:
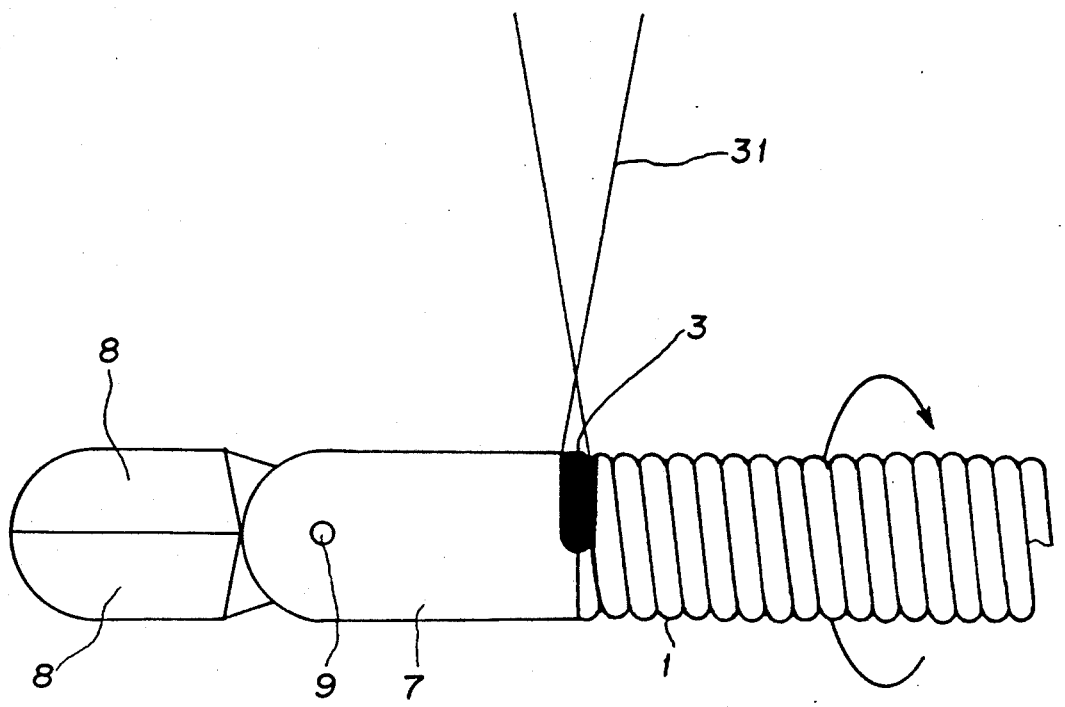
FIG. 18 is an enlarged, raised section showing a conventional forceps device in the vicinity of the leading end.
Figure 19:
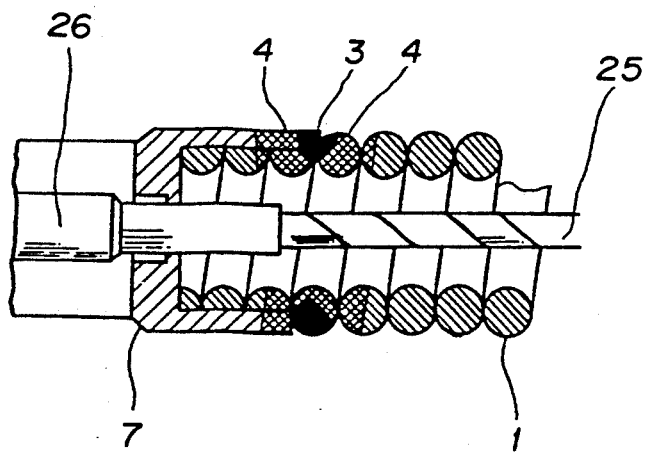
FIG. 19 is an enlarged section showing a conventional forceps in the vicinity of the leading end.
Figure 20:
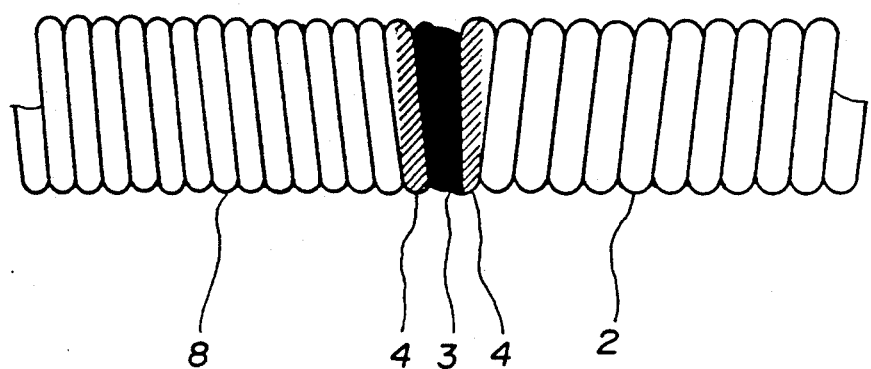
FIG. 20 is an enlarged, raised section showing a conventional forceps.
Figure 21:
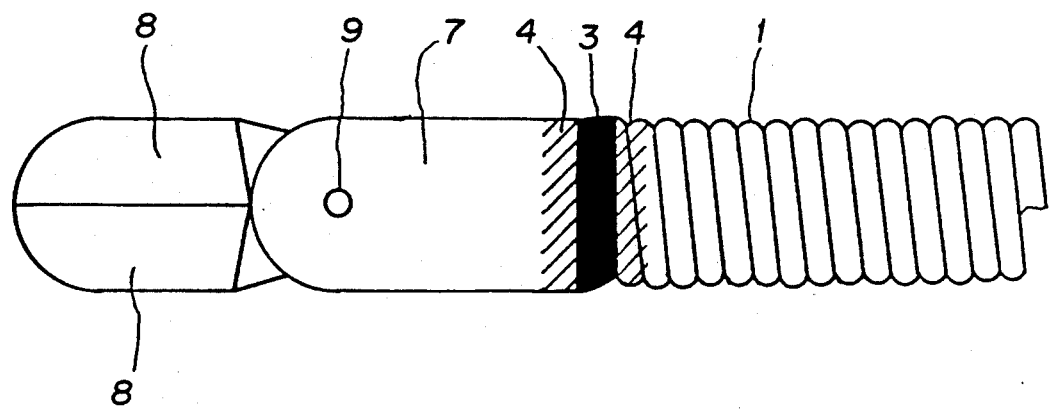
FIG. 21 is an enlarged, raised section showing a conventional forceps in the vicinity of the leading end.
Figure 22:
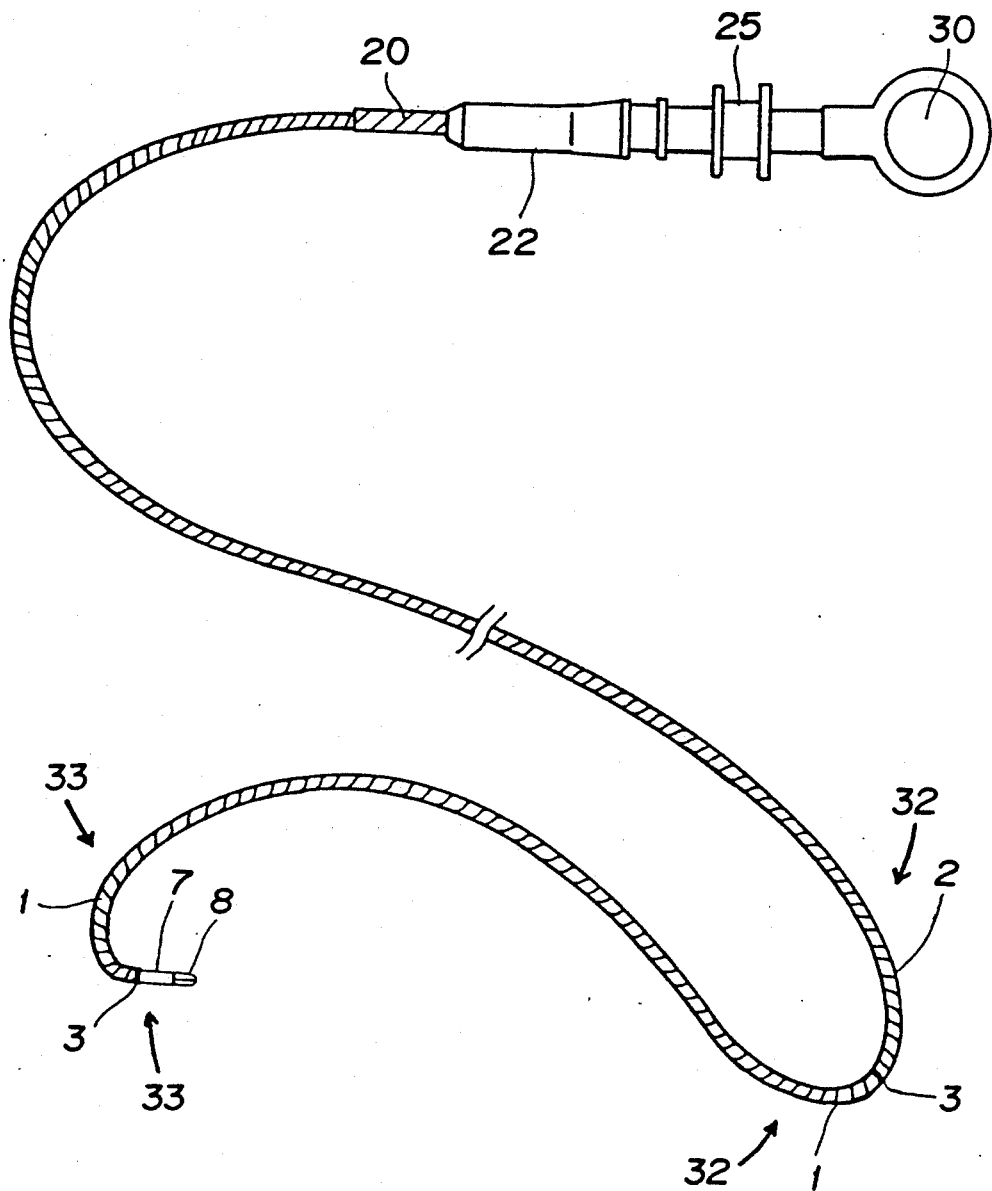
FIG. 22 is a raised sketch of a conventional forceps device.
Figure 23:
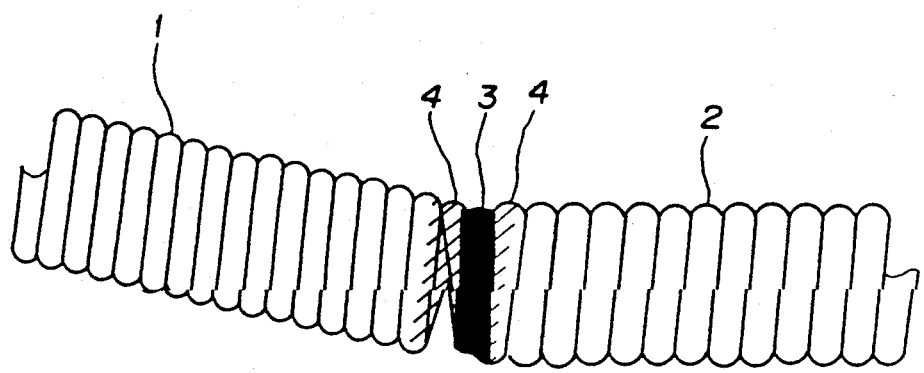
FIG. 23 is an enlarged, raised section showing a conventional forceps device.
Figure 24:
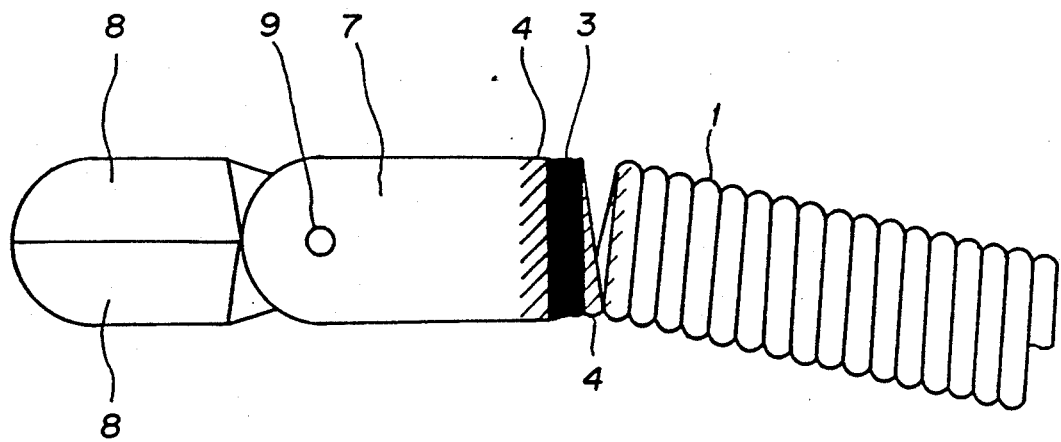
FIG. 24 is an enlarged, raised section showing a conventional forceps in the vicinity of the leading end.

Furthermore, as shown in FIG. 12, a laser beam may be irradiated onto a butted joint between a soft flexible tube (1) and a leading metal member (7) to form a continuously welded joint on the whole outer surface of the butted joint. Instead of the fully continuous welded joint, a partly continuous welded joint having a complementary unwelded portion, like the one shown in FIG. 9, is also allowable. As shown in FIG. 12, it is easy to form these, butted joints because there is no need to work the end portions of both the flexible tubing and the leading metal member to make them fit together.

In this embodiment, adjacent turns of the coil for the flexible tubing can be spot-welded in the same way as for the soft flexible tubing of the first embodiment.

What is claimed is:

1. A joint structure consisting of flexible tubing and another member; the flexible tubing is constructed of a metal wire element wound in to a coil; the joint structure comprises: 1) a welded joint joining the end of the outer peripheral surface of the flexible tubing to the end of the other member by welding all or part of the joint; and 2) spot welds joining together adjoining turns of the coil in the vicinity of the welded joint by irradiating a laser beam onto a number of separate spots extending over the adjoining turns.

2. A joint structure consisting of flexible tubing and another member, in accordance with claim 1, wherein one of the adjoining turns is the end of the outer peripheral surface of the flexible tubing.

3. A joint structure consisting of flexible tubing and another member, in accordance with claim 1, wherein the other member is a circular ring.

4. A joint structure consisting of flexible tubing and another member, in accordance with claim 1, wherein the other member is a second flexible tube constructed of a metal wire element wound into a coil.

5. A joint structure consisting of flexible tubing and another member, in accordance with claim 4, wherein the flexibility of the second flexible tube is higher than that of the first flexible tube.

6. A joint structure consisting of flexible tubing and another member, in accordance with claim 5, wherein the joint structure comprises spot welds joining adjacent turns of the coil of the second flexible tubing in the vicinity of the welded joint by irradiating a laser beam onto a plurality of separate spots extending over the adjoining turns.

7. A joint structure consisting of flexible tubing and another member, in accordance with claim 1, wherein the spot welds form a locus of continuous laser-beam weld spots.

8. A handling device for use in endoscopes, comprising one soft flexible tube and one hard flexible tube, each constructed of a metal wire element wound into a coil, the outer peripheral-surface ends of the flexible tubes being connected together by laser welding, adjoining turns of the coil of at least the soft flexible tube being joined together by means of laser spot welding at a number of spots, the adjacent turns including the turn at the joined ends.

9. A handling device for use in endoscopes, in accordance with claim 8, wherein the welded spots are separated.

10. A handling device for use in endoscopes, in accordance with claim 8, wherein the spots are continuous and overlap with one another.

11. A handling device for use in endoscopes, in accordance with claim 8, wherein the metal wire elements composing the flexible tubes are circular in section and the flexible tubes have equal outside diameters.

12. A handling device for use in endoscopes, in accordance with claim 8, wherein the metal wire elements composing the flexible tubes are circular in section and the flexible tubings have equal inside diameters.

13. A handling device for use in endoscopes, in accordance with claim 8, wherein the soft flexible tube is smaller in outside diameter and larger in inside diameter than the hard flexible tube.

14. A handling device for use in endoscopes in accordance with claim 8, wherein the hard flexible tube comprises a number of turns in a coil.

15. A handling device for use in endoscopes, comprising a flexible tube constructed of a metal wire element wound into a coil and a leading metal member, the outer peripheral-surface end of the flexible tubing and the leading metal member being joined together by laser welding, adjoining turns of the coil of the flexible tubing being joined together by means of laser spot welding at a number of spots, the adjoining turns including the turn at the connected surface end of the flexible tubing

16. A handling device for use in endoscopes, in accordance with claim 15, wherein the welded spots are separated.

17. A handling devices for use in an endoscopes, in accordance with claim 15, wherein the welded spots are continuous and overlap with one another.

18. A handling device for use in an endoscopes in accordance with claim 15, wherein the weld spots are on a plane perpendicular to the axis of the flexible tubing.

19. A handling device for use in endoscopes, in accordance with claim 15, wherein the weld spots are placed along the contact line between adjoining turns.

* * * * *